United States Patent [19]

Stautzenberger et al.

[11] Patent Number: 4,868,324

[45] Date of Patent: Sep. 19, 1989

[54] PURIFICATION OF DIPHENYL PHTHALATES

[75] Inventors: A. Lee Stautzenberger; Ellen A. Langford; Edward E. Quick, all of Corpus Christi, Tex.

[73] Assignee: Celanese Engineering Resins, Inc., Chatham, N.J.

[21] Appl. No.: 198,037

[22] Filed: May 24, 1988

[51] Int. Cl.$^4$ .............................................. C07C 67/60
[52] U.S. Cl. ...................................... 560/78; 560/79; 560/99
[58] Field of Search .............................. 560/78, 79, 99

[56] References Cited

U.S. PATENT DOCUMENTS 4,304,925  12/1981  Watanabe et al. .................... 560/78
4,464,477  8/1984   Bunger et al. ..................... 560/78 X Primary Examiner—Werren B. Lone
Assistant Examiner—Vera C. Clarke
Attorney, Agent, or Firm—Depaoli & O'Brien

[57] ABSTRACT

Crude diphenyl phthalates, including isomeric mixtures thereof which are prepared by reacting mixtures of isophthalic and terephthalic acids with phenol, preferably in the presence of an organotitanate, organozirconate, or organostannate catalyst, are purified by dissolving the crude phthalate in an organic solvent, contacting the resulting solution with dilute aqueous alkali to neutralize the ester, separating the resulting oil and aqueous phases, and thereafter recovering from the oil phase a purified diaryl phthalate of reduced color and low acidity.

11 Claims, No Drawings

PURIFICATION OF DIPHENYL PHTHALATES

BACKGROUND OF THE INVENTION

1. Field of the Invention

This invention relates to the purification of esters and especially the purification of diaryl esters of dicarboxylic aromatic acids, such as diphenyl phthalates and dicresyl phthalates.

2. Review of the Prior Art

The production of various phenolic esters of aromatic carboxylic acids, such as diphenyl terephthalate and diphenyl isophthalate, has become of significant commercial interest in recent years due to their use in a great many types of processes. For example, diphenyl terephthalate and diphenyl isophthalate dissolved in a solvent may be reacted with a primary diamine to produce polyamides. However, despite the importance of these phenolic esters, no processes have been developed for their production that are satisfactory as to both price and performance. For example, expensive aroyl reactants can be used to prepare the esters, or multiple distillations may be employed for product purification, but the products are then overpriced for market usage.

Crude diphenyl phthalates made by direct esterification or by exchange reactions are pink to brown colored, having an APHA color of up to 500 and acid no. 4, for example, acid number being defined as mg KOH/g. Crude diphenyl phthalates are difficult to purify to the extent needed for many applications such as the production of polycondensation products and particularly high quality resins. These uses require diphenyl phthalates which are colorless or at least of low color (e.g., APHA 10 and at least less than APHA 40) and have a low acid number (e.g., acid no. 0.01 and at least less than 0.2 mg KOH/g.)

This coloration cannot be completely removed, thereby obtaining specification quality diphenyl phthalates, by vacuum distillation, by recrystallizing the ester from solvents such as aromatic hydrocarbons, or by using adsorbents, such as activated carbons, charcoal, or activated fullers' earth.

Methods involving the addition of a solvent for purifying the ester, followed by subsequent phase separation, have been troubled with formation of emulsions and gelatinous precipitates. Other, methods involving heat transfer, such as vacuum distillation, create additional difficulties because of the very high melting point of the diphenyl terephthalate of 199°-200° C.

One purification technique for the reaction product of aromatic carboxylic acids with aliphatic alcohols, as described in U.S. Pat. No. 4,304,925, comprises the addition of water at 5-50% by weight, heating at reflux until the organo titanium compound used as catalyst is hydrolyzed, adding a basic substance, such as hydroxides, carbonates, or bicarbonates of alkali metals, separating the esterification reaction mixture from the aqueous layer, further purifying, if desired, by washing with water and subsequently separating the aqueous layer, and distilling under reduced pressure or at elevated temperatures or by treating with activated clay, activated carbon, diatomaceous earth, or the like. The aromatic carboxylic acids include phthalic acid, isophthalic acid, terephthalic acid, trimellitic acid, hemimellitic acid, and trimesic acid.

A difficulty with such a purification method is that the ester product must be cooled below 100° C., thereby often causing phase separation difficulties between the ester phase and the aqueous phase with consequent loss of product on phase separation. Particularly when titanium compounds are used as esterification catalysts, the use of aqueous alkali hydrolyzes the metal compound to produce a gelatinous precipitate which tends to aggravate the loss of product when organic or aqueous phases are separated. Furthermore, if alcohol removal is attempted by blowing steam through the reaction product at a temperature in excess of 100° C. without first removing the esterification catalyst, a titanium catalyst can be hydrolyzed to a difficultly separable gel, as discussed in U.S. Pat. No. 3,818,071.

A method for purifying a solution of dimethyl terephthalate in a water-insoluble organic solvent, such as chloroform, comprises passing the solution through a column in concurrent or countercurrent flow to a dilute aqueous solution of sodium hydroxide, as taught in U.S. Pat. No. 2,753,369.

U.S. Pat. No. 2,656,377 teaches the separation of isophthalate and terephthalate di-esters from a mixture thereof by adding any two different solvents capable of dissolving different ratios of the isophthalate and the terephthalate. Xylene is a suitable solvent of lower solubility ratio.

U.S. Pat. No. 3,277,153 relates to a process for the preparation of diphenyl carboxylic acid methyl esters from distillation residues obtained in the production of tere- and/or isophthalic acid dimethyl esters. After re-esterification, the residues are dissolved in hot xylene or methanol, and the diphenyl carboxylic acid methyl esters are obtained by repeated crystallization from the solvent.

U.S. Pat. No. 3,600,430 relates to a process for purification of a diester of a benzenedicarboxylic acid, e.g., bis(2-hydroxyethyl) terephthalate, by adding thereto mixed xylene solvent (Example II). The preferred amount of solvent is such that the ratio of diester dissolved in the solvent, i.e., the lighter phase, to the diester in the heavy or molten diester phase is less than about 48:1 and preferably less than about 24:1. The phases are separated, and purified diesters are recovered from the lighter phase.

A specific purification method is disclosed in U.S. Pat. No. 3,705,186 for producing pure, colorless diphenyl terephthalate. It begins with transesterification of dialkyl terephthalates with at least equivalent amounts of phenyl acetate in the presence of butyl titanate as a catalyst by (a) heating the dialkyl terephthalate with phenyl acetate in an inert atmosphere in the presence of 1-5 wt. % of activated carbon to temperatures above 150° C., (b) then adding the titanic acid ester, (c) immediately removing the alkyl acetate, (d) stirring the hot carbon-containing crude ester into a relatively high boiling aromatic hydrocarbon, such as xylene, under an inert gas, and (e) crystallizing the product after removing activated carbon by filtering.

U.S. Pat. No. 4,464,477 relates to a process for recovery and reuse of heavy metal oxidation catalyst from distillation residues in the production of dimethyl terephthalate by oxidation of p-xylene and methyl p-toluate. The distillation residue feed is mixed with aqueous extractant. The resulting emulsion is settled, and the organic phase therefrom is mixed with the waste water extractant from the oxidation process and settled again to obtain the extractant as the aqueous phase. Xylenes can be added to the organic phases in order to lower viscosity.

All of these purification methods involve losses of product, difficulties with filtering or phase separation, or the use of expensive additives such as activated carbon. Accordingly, there is a need for a simpler, easier, and less expensive purification process for diaryl esters such as diphenyl phthalates.

SUMMARY OF THE INVENTION

It is therefore an object of this invention to provide a process for purifying crude diphenyl phthalate esters in which the esters are separated from most coloring materials without significant loss of product.

It is also an object to provide such a process wherein phase separation occurs between an aqueous phase and an organic oil phase, whereby separation difficulties do not occur and the purified ester product is not significantly lost to the aqueous phase.

In accordance with these objectives and the principles of this invention, it has surprisingly been discovered that crude diphenyl phthalate esters may be readily purified by dissolving the crude impure diesters in a suitable solvent, contacting the resulting solution with dilute aqueous alkali to neutralize the ester, separating the resulting organic oil and aqueous phases, and thereafter recovering from the oil phase a purified diphenyl phthalate ester of reduced color and low acidity which is suitable for many purposes. The purified diphenyl phthalates, for example, are eminently suited for the preparations of high quality polyarylate engineering resins by reaction with bisphenol A.

In carrying out the invention crude diphenyl esters, such as diphenyl isophthalate, are dissolved in a suitable inert organic solvent, preferably a hydrocarbon or chlorinated hydrocarbon solvent such as benzene, a xylene or methylene chloride. Other solvents suitable for use include mixtures of ortho, meta and para-xylene, ethylbenzene, cumene, toluene, o-chlorotoluene, chlorobenzene, 1,2,3-trimethylbenzene, 1,3,5-trimethylbenzene, n-propylbenzene, 1,3-dichlorobenzene, etc. The preferred solvent is a xylene.

The solvent is advantageously heated to a temperature of about 90° C. to 110° C. to completely dissolve the crude phenolic ester.

The amount of solvent is not critical and the amount thereof should be sufficient to completely dissolve the phenolic ester. The amount of the crude diester in any given liquid solvent should be such that the solubility limits of the ester are not exceeded.

After dissolving the crude phenolic ester in the solvent the resulting solution is contacted with an aqueous solution of alkali which neutralizes the acid in the ester (free or monoester). The alkali also neutralizes any free phenol and carries it into the aqueous phase. As a result, two liquid phases will form, an organic oil phase which will be comprised mainly of a solution of diester in the solvent, and an aqueous phase which contains alkali and color impurities. Phase separation is preferably carried out at temperatures near the temperature of the heated solvent, e.g., 90° C. to 110° C., and surprisingly the phases separate quickly and clearly without the formation of emulsions, gelatinous precipitates, or slime.

Suitable alkali solutions are sodium and potassium hydroxide which are used in an amount sufficient to neutralize acid in the ester, usually about two-fold excess based on the acid number (mg KOH/g sample) of the ester. Alkali solutions of sodium carbonate, potassium carbonate, lithium carbonate, sodium bicarbonate, potassium bicarbonate, and the like may be used but are less preferred. Similarly an alcoholic solution of alkali may be employed if desired.

The preferred alkali solution is a dilute aqueous 0.1 to 0.5 normal solution of sodium hydroxide. Neutralization is preferably carried out at an elevated temperature of about 100° C.

Following separation of the phases the oil phase is cooled to precipitate crystals of diester and filtered to recover the ester filter cake which is then washed essentially free of ions, dried and vacuum distilled. Washing may be accomplished with water (preferably with distilled water and conveniently in the filter) or a lower alkanol of one to four carbon atoms such as isopropanol. After washing is complete, the filter cake is dried in a rotary drier or vented oven or preferably a vacuum oven at a temperature between about 25° C. and 150° C.

Flash distillation of the filter cake is thereafter carried out in a conventional manner at temperature of 225° C. to 260° C. under subatmospheric pressure of about 0.5 to 3 torr. Prior to flash distillation, $K_2CO_3$ or other alkali, as above noted, may be added to the ester in slight excess over any acidity (acid number) of the filter cake.

The phenolic esters which are purified in accordance with the invention are derived from aromatic carboxylic acids which should be essentially free of aldehydic and ketonic carbonyl groups as these groups interfere with the esterification reaction. Other than these aldo and keto groups, the aromatic carboxylic acid many contain various functional groups which do not interfere with the esterification reaction. Generally the aromatic carboxylic acid will contain no functional groups or radicals other than carboxyl, carboxylic ester, ether, thioether, aromatic ring-substituted halo, sulfo, or sulfonyl. The aromatic carboxylic acids which are free of ketonic and aldehydic carbonyl groups have the formula:

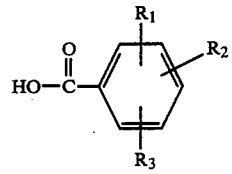

wherein $R_1$ and $R_2$ are alike or different and correspond to hydrogen, carboxyl or hydroxy and wherein $R_3$ is hydrogen or an organic radical of six to 20 carbon atoms containing an aromatic ring, which organic radical is composed only of elements selected from the groups consisting of carbon, hydrogen, and oxygen.

Especially preferred are those dicarboxylic acids of the formula

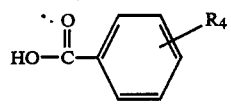

where $R_4$ is carboxyl group or a radical of seven to 20 carbon atoms of the formula

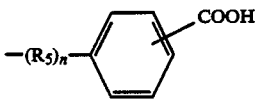

wherein n is 0 or 1 and $R_5$ is a divalent hydrocarbon radical, oxygen, or a divalent radical composed of carbon, hydrogen, and oxygen wherein the oxygen present is as an ether linkage. Among the acids containing aromatic ring-substituted carboxyl groups that are preferred are benzoic acid, phthalic acid, terephthalic acid, isophthalic acid, diphenic acid, homophthalic acid, toluic acid, alpha-naphthoic acid, chlorobenzoic acid, salicylic acid, 1,2-(ethylenedioxy) dibenzoic acid, and 2,5-dimethylterephthalic acid. Mixtures (3/1) of iso- and terephthalic acid are especially preferred.

The phenols utilized for production of the esters are monofunctional phenols which contain only one phenolic hydroxyl group. Generally these phenols will be those of six to 15 carbon atoms of the formula

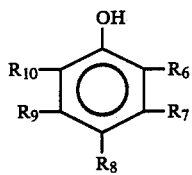

wherein $R_6$, $R_7$, $R_8$, $R_9$ and $R_{10}$ may be hydrogen, alkyl, alkaryl, aryl, or aralkyl radicals. Among the particular phenols that may be utilized are phenol, o-cresol, m-cresol, p-cresol, xylenols, either mixed or the pure isomer, o-phenylphenol, and p-phenylphenol. Of the various phenols that may be utilized, phenol itself is preferred over the others.

The reaction of the aromatic carboxylic acid with phenol in the presence of a catalyst is a known reaction which is carried out in the liquid phase in a customary manner using equipment normally used for esterification reactions. The organic carboxylic acid is reacted with an excess of the phenol. The reaction conditions can be varied depending upon the type of esters being formed and the particular phenol being employed. A temperature sufficient to effect esterification in the presence of the catalyst is used and generally at temperatures ranging between 230° C. and 300° C. Catalysts which may be employed for esterification include organotitanates, organozirconates and organostannates.

The process may be more clearly understood by referring to the following examples which illustrate the best mode now contemplated for carrying out the invention.

EXAMPLE 1

Phenol was reacted with a 3/1 mixture of iso- and terephthalic acids using an organozirconate catalyst (an organotitanate catalyst or an organostannate catalyst would have been equally satisfactory), and then 353 grams of the resulting crude diphenyl esters of the phthalates were dissolved in 940 ml of m-xylene. This solution was mixed with about 600 ml of 0.5N NaOH in a 3-liter pot with agitation at 95° C. for one hour. The mixture was then transferred to a heated separator in which the organic phase was separated from the aqueous phase. The organic phase was then allowed to cool to room temperature. The precipitated crystals were recovered by centrifuging to remove the supernatant liquor.

EXAMPLE 2

The above procedure was repeated and 354 grams of the same crude diphenyl esters were dissolved in 940 ml of m-xylene to form a solution which was mixed with 500 ml of 0.5N NaOH for one hour at 95° C. under vigorous agitation. The blended mixture was then placed in a heated separatory funnel, having a volume of about 600 ml, from which the aqueous phase was drawn off. The organic phase was placed in a separate flask. The solutions were made up in three batches, the first being mostly organic and the organic phase being dark. The second batch was approximately equally organic and aqueous, the organic phase being very light. The thid batch was almost all aqueous, but the organic phase was very light. The organic phases were combined and allowed to cool. The resulting crystals were then separated from the mother liquor by centrifuging.

The batches of crystals as prepared above were charged into a one-liter distillation flask after having been dried overnight. The pot temperature was gradually increased to approximately 250° C. in one hour and 40 minutes, 0.5 g of $K_2CO_3$ having been initially added. The pressure in the flask was about 1.8 mm Hg. The distillate was collected in three flasks. One flask contained 27.04 g and had a color of APHA 20 and an acid number of 0.01. Another flask contained 442.15 g and had a color of APHA 10 and an acid number of less than 0.01. The last flask contained 12.1 grams and had a color of APHA 10 and an acid number of 0.01. Recovery was 96.6% by weight of the charged crude diphenyl phthalates.

What is claimed is:

1. A method for purification of a crude diphenyl ester of an aromatic dicarboxylic acid which comprises dissolving said ester in an inert organic hydrocarbon solvent, contacting the resulting solution with dilute aqueous alkali to neutralize free phenol and acid in the ester and form an organic oil phase comprising diester and solvent and an aqueous phase containing alkali, neutralized free phenol and acids and color impurities, separating the oil and aqueous phases, and thereafter recovering from the oil phase a purified diphenyl ester of reduced color and low acidity.

2. The method of claim 1 wherein the diphenyl ester is selected from the group consisting of the diphenyl ester of isophthalic acid, the diphenyl ester of terephthalic acid and mixtures thereof.

3. The method of claim 2 wherein the diphenyl esters are prepared from the reaction of phenol with a 3/1 mixture of iso- and terephthalic acid in the presence of a catalyst selected from the groups consisting of organotitanate, organozirconate, and organostannate catalysts.

4. The method of claim 3 wherein the hydrocarbon solvent is a xylene.

5. The method of claim 4 wherein the oil phase is cooled to precipitate crystals of diphenyl ester.

6. A method for purification of a crude diphenyl ester of an aromatic dicarboxylic acid which comprises dissolving said ester in an inert organic hydrocarbon solvent at temperatures of about 90° C. to 110° C., contacting the resulting solution with a dilute aqueous alkali for a period of time sufficient to neutralize free phenol and acid in the ester and form an organic oil phase containing the ester and solvent and an aqueous phase containing alkali neutralized free phenol and acids and color impurities, separating the oil and aqueous phases at temperatures of about 90° C. to 110° C., cooling the oil phase to precipitate crystals of diphenyl ester, and thereafter distilling said ester under subatmospheric pressure at a temperature of about 225° C. to 260° C. to obtain diphenyl ester of reduced color and low acidity.

7. The method of claim 6 wherein the solvent is a xylene.

8. The method of claim 7 wherein the precipitated crystals of diphenyl ester are washed free of ions and dried prior to distillation.

9. The method of claim 7 wherein the pressure is 0.5 to 3 torr.

10. The method of claim 9 wherein the diphenyl ester is selected from the group consisting of the diphenyl ester of isophthalic acid, the diphenyl ester of terephthalic acid and mixtures thereof.

11. The method of claim 10 wherein the diphenyl esters are prepared from the reaction of phenol with a 3/1 mixture of iso- and terephthalic acid in the presence of a catalyst selected from the group consisting of organotitanate, organozirconate and organostannate catalysts.

* * * * *